United States Patent [19]

Sherwood

[11] Patent Number: 5,686,491

[45] Date of Patent: Nov. 11, 1997

[54] INFANT FORMULA

[75] Inventor: Geoffrey Sherwood, Dallas, Tex.

[73] Assignee: Sigma-Tau Pharmaceuticals, Inc., Gaithersburg, Md.

[21] Appl. No.: 305,602

[22] Filed: Sep. 14, 1994

[51] Int. Cl.$^6$ .................................................. A61K 31/195
[52] U.S. Cl. ..................... 514/561; 514/7; 514/23; 514/60; 514/556; 514/560
[58] Field of Search ................................ 514/556, 560, 514/7, 23, 60, 561

[56] References Cited

U.S. PATENT DOCUMENTS

| | | | |
|---|---|---|---|
| 4,753,926 | 6/1988 | Lucas et al. | 514/2 |
| 4,920,098 | 4/1990 | Cotter et al. | 514/2 |

OTHER PUBLICATIONS

Medline Abstract, AN:87209982, (Jun. 1987), Winter, S.C. et al., Am J Dis Child, (Jun. 1987) 141(6) pp. 660–665.

*Primary Examiner*—Marianne M. Cintins
*Assistant Examiner*—M. Moezie
*Attorney, Agent, or Firm*—Oblon, Spivak, McClelland, Maier & Neustadt, P.C.

[57] ABSTRACT

The present invention provides an infant formula for infants with metabolic disorders in fatty acid catabolism such as medium-chain acyl-CoA dehydrogenase deficiency (MCAD), long-chain acyl-CoA dehydrogenase deficiency (LCAD), short-chain acyl-CoA dehydrogenase deficiency (SCAD), multiple acyl-CoA dehydrogenase deficiency (MADD), Sudden Infant Death Syndrome (SIDS) and failure to thrive syndrome. The present invention also provides an assay for diagnosing children and infants with metabolic disorders such as failure to thrive syndrome; a method for treating failure to thrive syndrome; and a process for normalizing the lipid content of the mitochondrial membrane. In particular, the present invention provides an infant formula containing 90–130 cals/Kg which comprises (a) 2.5–3.5 g/Kg protein; (b) carbohydrate; (c) fat; and (d) $\geq 500$ mg carnitine, wherein the ratio of carbohydrate to fat is greater than or equal to 60:40.

19 Claims, 3 Drawing Sheets

INFANT FORMULA

BACKGROUND OF THE INVENTION

1. Field of the Invention

The present invention provides an infant formula for infants with metabolic disorders in fatty acid catabolism such as medium-chain acyl-CoA dehydrogenase deficiency (MCAD), long-chain acyl-CoA dehydrogenase deficiency (LCAD), short-chain acyl-CoA dehydrogenase deficiency (SCAD), multiple acyl-CoA dehydrogenase deficiency (MADD), some cases of Sudden Infant Death Syndrome (SIDS) and Failure to Thrive Syndrome (FTTS). The present invention also provides an assay for diagnosing children and infants with metabolic disorders such as FTTS; a method for treating FTTS; and a process for normalizing the lipid content of the mitochondrial membrane.

2. Discussion of the Background

The development of substitutes for maternal milk is an integral part of the history of pediatrics. Although no infant formula has been developed that reproduces the immunologic properties and digestibility of human milk, infant formulas have gone through many revisions and have become an important part of the feeding regimen of many infants in their first year. When used as the sole source of nourishment, infant formula must meet all the energy and nutrient requirements for healthy term infants for the first 6 months of life. Standards for infant formulas in the United States are developed by the American Academy of Pediatrics Committee on Nutrition.

Approximately half of all infants born in the United States in 1990 received a commercially prepared formula in the hospital despite pediatrician recommendations for breast-feeding. Commercial infant formulas continue to play a substantial role in meeting the nutrient needs of infants in the United States. It is estimated that by 2 months of age, 72% of all infants receive prepared formulas. When all types of milk feeding during the first year of life were considered, breast-feeding accounted for 19%, commercial infant formulas for 64%, and cow's milk and evaporated milk for 23% (Montalto MB et al, *Pediatrics* (1985) 75:343–351; Martinez GA et al, *Am. J. Dis. Child* (1985) 139:1010–1018).

Another component of the diet of infants in the United States is supplemental foods such as cereal or pureed foods. By 6 months of age, approximately 25% of the infant's caloric intake is derived from prepared infant foods or pureed home foods. At 12 months, only 35% of the total energy intake is derived from milk; most of the remainder is derived from table foods.

The composition of infant formulas has evolved over many years. Human milk serves as a model for infant formulas. Early infant formulas consisted of whole or evaporated cow's milk, sugar, and water. Most infants have thrived on these formulas; a few, however, have displayed signs and symptoms of formula intolerance. Consequently, research to improve the acceptability and quality of infant formulas continues. In addition to formulas used for feeding healthy term infants, a number of special-purpose formulas are available for infants with gastrointestinal or metabolic disturbances (Klish WJ, *Pediatrics in Review* (1990) 12:55–62; MacLean WC & Benson JD, *Semin. Perinatol.* (1989) 13:104–111).

The compositions of commercial infant formulas, in particular the percentages of protein, fat and carbohydrate, are extremely varied and often depend on the manufacturer's research and development results, marketing strategy and consumer preferences. Standard infant formulas have a protein content which is much higher than that found in human milk; the fat is largely saturated, poorly absorbed, and contains little essential fatty acids; and the carbohydrate is a mixture of lactose and sucrose. These formulas are prescribed with a caloric density of 67 to 70 kcal/dL (20 kcal/oz), similar to human milk, and can be offered ad libitum. The usual intake is 150 to 200 mL/kg/d. This provides 100 to 135 kcal/kg/d and typically results in weight gain of 20 to 30 g/d.

Protein is typically provided as whey. Some manufacturers add cow's milk whey with reduced minerals to skim cow's milk to achieve a ratio of 60% whey and 40% casein protein; other manufacturers use unaltered cow's milk protein which is 18% whey and 82% casein. Most of the milk-based formulas in the United States contain at least 50% more protein than human milk (1.5 g/dL vs 0.9 to 1.0 g/dL). U.S. Pat. No. 4,879,131 describes infant formula containing whey products in an amount of from 0.5% to 5% by weight of the total composition.

Fats usually provide approximately 40% to 50% of the energy in formulas. Whereas human milk contains cholesterol; fat in formulas is typically provided as vegetable oils and contain little or no cholesterol. Butterfat from cow's milk is typically substituted with vegetable oils or blends of vegetable oil and animal fats to improve fat digestibility, to provide for essential fatty acids, and to reduce environmental contaminants. Fat blends are conventionally selected to provide a balance of saturated and unsaturated fatty acids. Coconut oil provides an excellent source of highly digestible saturated fatty acids of relatively short chain length; whereas soy, oleo, corn, and safflower oil provide an abundant source of polyunsaturated fatty acids. U.S. Pat. No. 3,542,560 disclose fat compositions for infant formulas having an increased portion of the palmitic acid in the beta position of the triglyceride. U.S. Pat. Nos. 4,282,265; 4,614,663 and 4,721,626 describe infant formula compositions containing palm oil.

Some manufacturers use a genetic variant of safflower oil to increase mono-unsaturated fatty acids in the fat blend. The essential fatty acids, linoleic acid and $\alpha$-linolenic acid, are typically provided in ample concentration in human milk and formulas. The optimal ratio linoleic acid to $\alpha$-linolenic acid in formulas was described by Clark KJ et al, *J. Pediatrics* (1992) 120:S151–S158.

Conventional infant milk formulas provide non-protein calories in the ratio of 60:40 carbohydrate to lipid. However, in recent years, the trend in the infant milk formula industry has been to provide an increasing array of high caloric density preparations (30 cals/oz). These includes PEDIASURE (available from Ross), ENRICH (available from Ross), ENSURE (available from Ross), ENSURE PLUS (available from Ross), OSMOLITE (available from Ross), ISOCAL (available from Mead Johnson Nutritionals), SUSTACAL (available from Mead Johnson Nutritionals), etc. In these products the total caloric intake and the absolute quantity of lipid ingested is increased. These high caloric density preparations are commonly provided to promote and maintain growth in infants with metabolic disorders or with FTTS.

Unfortunately, certain infants do not respond to such formulas. In particular, when infants and children with metabolic disorders in fatty acid catabolism are treated with preparations containing an increased lipid content, no clinical improvement is obtained.

Figure 1:
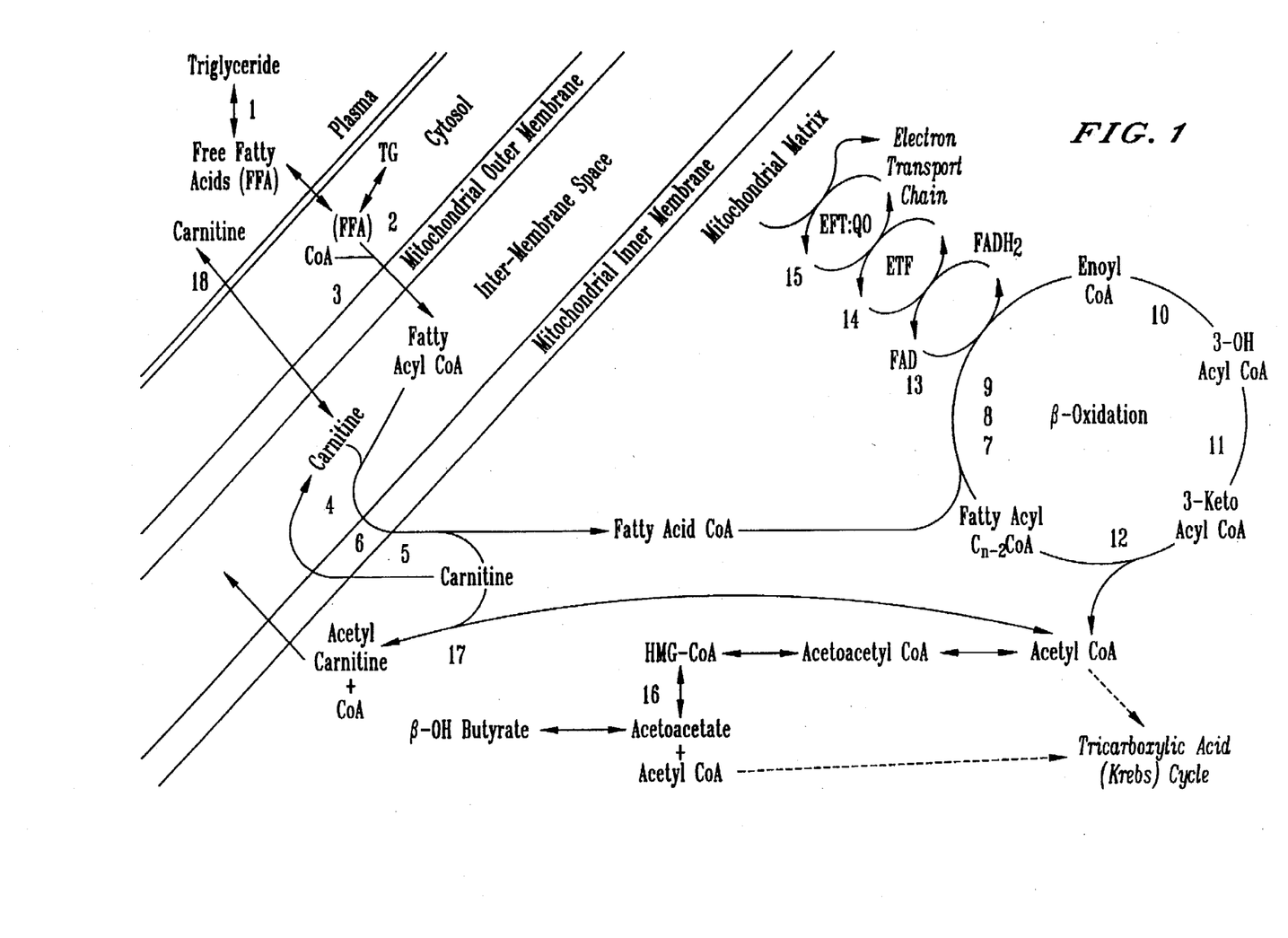
FIG. 1 illustrates the metabolic cascade from triglycerides to the final product ATP.
Figure 2A:
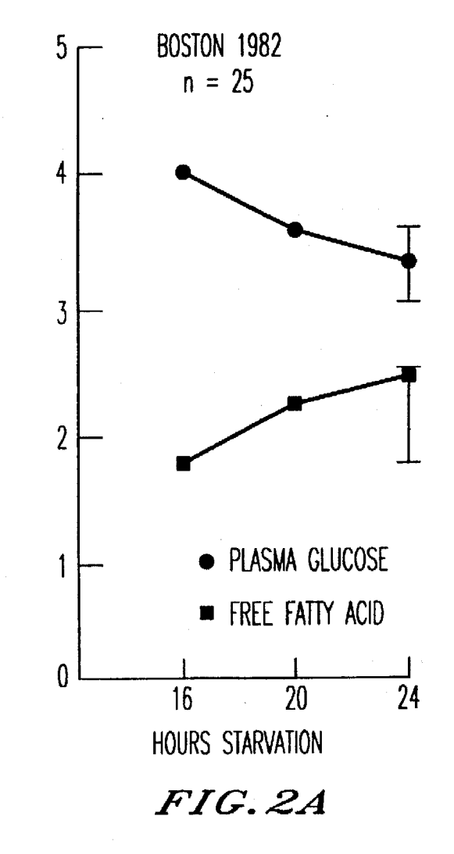
FIG. 2 are charts of the plasma glucose (●) and free fatty acid (■) profiles in healthy infants, infants with starvation ketosis and infants suffering from failure to thrive syndrome.
Figure 2B:
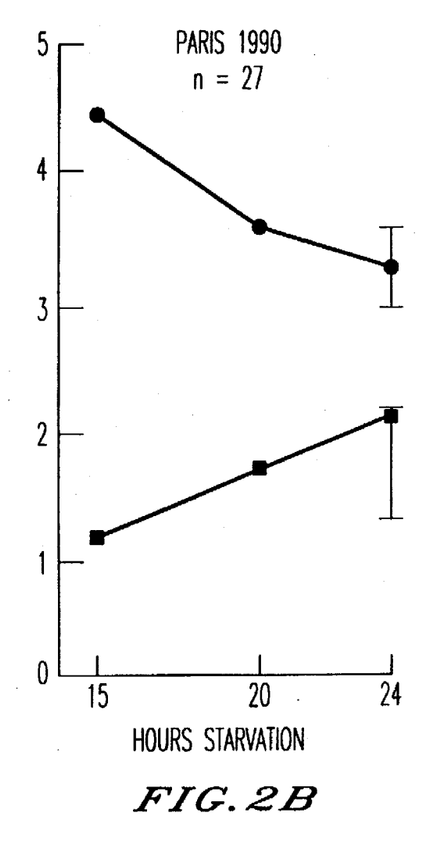
Figure 2C:
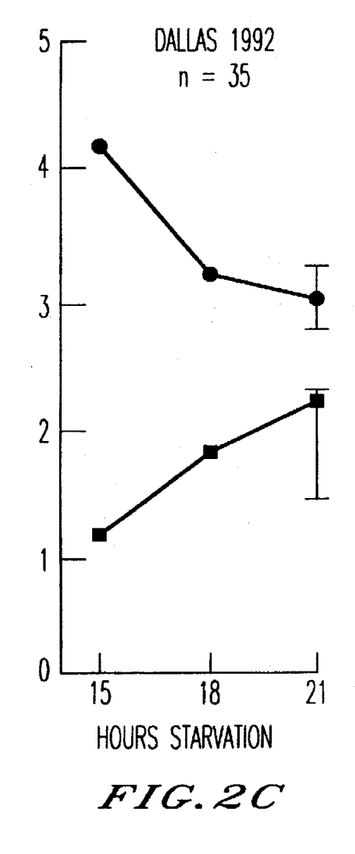
Figure 3A:
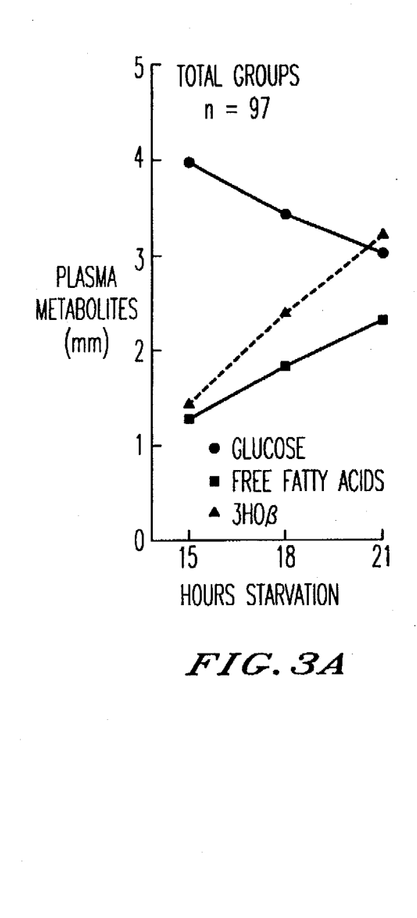
FIG. 3 are charts of the plasma metabolites (mM) after 15, 18 and 21 hours of fasting in 97 cases: glucose (●), free fatty acid (■) and 3-hydroxybutyrate (o).
Figures 3B, 3C:
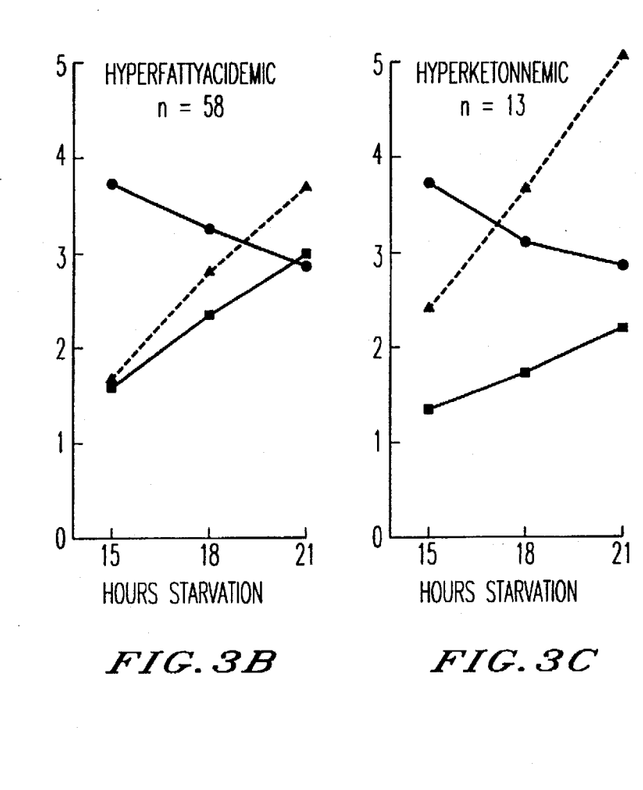
Figure 3D:
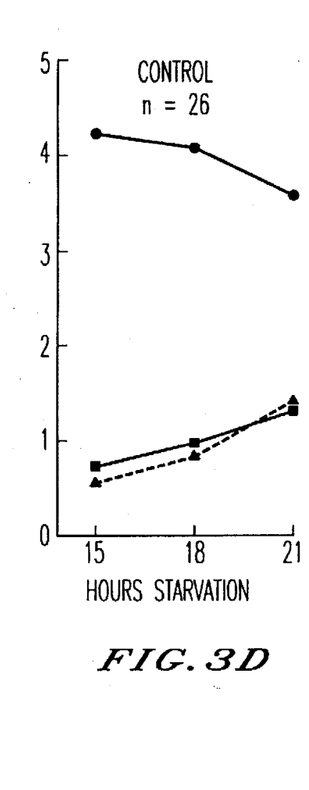

The metabolic cascade from triglycerides to the final production of ATP is shown in FIG. 1. Known metabolic defects are numbered (Table 1).

| ENZYMES/PROTEINS INVOLVED IN FATTY ACID OXIDATION | |
|---|---|
| 1. | Lipoprotein lipase |
| 2. | Fatty acid binding protein |
| 3. | Fatty acyl CoA synthetase |
| 4. | Carnitine palmitoyl transferase I (CPT I) |
| 5. | Carnitine palmitoyl transferase II (CPT II) |
| 6. | Fatty acylcarnitine translocase |
| 7. | Long-chain acyl-CoA dehydrogenase (LCAD) |
| 8. | Medium-chain acyl-CoA dehydrogenase (MCAD) |
| 9. | Short-chain acyl-CoA dehydrogenase (SCAD) |
| 10. | Enoyl CoA hydratase |
| 11. | 3-hydroxy acyl-CoA dehydrogenase |
| 12. | 3-ketoacyl-CoA thiolase |
| 13. | Flavin adenine dinucleotide (FAD) |
| 14. | Electron transfer flavoprotein (ETF) |
| 15. | ETF:coenzyme Q oxidoreductase (ETF:QO) |
| 16. | 3-hydroxy,3-methylglutaryl-CoA lyase (HMGCoA) |
| 17. | Carnitine acetyltransferase |
| 18. | Carnitine transport |

The disorder which is most common in this system appears to be MCAD deficiency. The typical presentation is a Reye-like illness in a 6–24 month old, an unusual age for classic Reye syndrome. The prodrome is short of non-existent, and the child progress rapidly from vomiting and lethargy to severe coma. Hypoketotic hypoglycemic and abundant dicarboxylic aciduria are important clues. As many as five percent of sudden infant deaths may be due to this or other fatty acid catabolic defects. Plasma free carnitine is likely to be low, and specific medium-chain fatty acylglycine and acylcarnitine conjugates are usually excreted (i.e., hexanoylglycine, suberylglycine, and octanoylcarnitine); so far, phenylpropionylglycine has invariably been present. There is a wider spectrum of clinical presentation in LCAD than in MCAD. Young patients may have recurrent Reye-like illnesses with hypoketotic hypoglycemia. Some have skeletal muscle involvement or cardiomyopathy. Older patients are now recognized with late onset myopathy and recurrent myoglobinuria. No characteristic biochemical markers are known, although patients are generally carnitine deficient. Most cases of SCAD have been infants with failure to thrive, recurrent vomiting without hypoglycemia, hypotonia, marked development delay and early demise. The urine organic acid profile is characterized by intermediates of short-chain fatty acid metabolism: ethylmalonic, adipic, butyric and methylsuccinic acids, and butyrylglycine.

MADD is a group of disorders which are still without resolution. The defects are at the level of entry of the electrons into the electron transport chain from several amino acids as well as from all three acyl-CoA dehydrogenases. Defects of transport, processing or binding of FAD, and specific deficiencies of ETF or the ETF:QO are all possible. Three forms are generally recognized with obvious clinical overlap between groups, and genetic heterogeneity within each group.

SIDS also called Cot or Crib Death is generally conceived as due to an anatomical functional immaturity of the neural networks that control vital functions such as heart rate and respiratory patterns. It is estimated that 3% of SIDS are due to metabolic disorders. Evidence is accumulating to indicate that abrupt increases in free fatty acids of one sort or another is the major factor that causes unexpected disruption of the control of vital function. The concept of metabolic SIDS began in the mid-1980s with the recognition of the association between SIDS and an inherited defect of one of the 10 or so sequential enzymes of fatty acid oxidation system. Infants with nonspecific failure to thrive are often determined to have low plasma carnitine levels.

FTTS is an expression used to categorize infants and children who fail to meet, or are below the standards for their age. These infants and children have values for height and weight below the fifth percentile on the NCHS Growth Chart. No current objective test is available to diagnose these infants and children. The term is equally applicable to physical and mental delay, although rarely applied to the latter. The etiology of this syndrome is varied and includes a host of physical deficiencies. Most children diagnosed with failure to thrive are initially seen because of an intercurrent illness such as diarrhea or recurrent vomiting. The children are frequently temperamental and difficult to care for. The children often demonstrate one or more of the following symptoms: placid inactivity; passive disinterest; poor appetite with recurrent regurgitation/vomiting; petite size with adequate adipose tissue mass (camouflaging poor muscle mass); modestly delayed motor development; excessive irritability/lethargy following routine immunization and intercurrent infections often associated with atypical febrile seizures.

There is an intimate relationship between the enzyme defects of fatty acid catabolism and carnitine metabolism. Carnitine is required for the transport of fatty acids into mitochondria for beta oxidation (FIG. 1). Further, when abnormal acyl-CoA compounds accumulate (as they do in many fatty acid and organic acidopathies), they bind to carnitine, forming abnormal acylcarnitine compounds which are then excreted in the urine. This process can deplete carnitine stores to such an extent that symptoms of carnitine deficiency may dominate the clinical picture and thus aggravate the underlying primary metabolic abnormality. Recent reports suggest that a major pathway for fatty acid incorporation into membranal phospholipids involves carnitine dependent acyl transferases present in all membranes. This pathway may turn out to be more important than the classical choline dependent pathway. Thus, it is plausible that excessive fat in previously consumed diets superimposed on partially impaired FAO resulted in a depletion of total body carnitine reserves thus creating a conditional essentiality for carnitine in normalizing membranal phospholipids.

The majority of the above disorders can be diagnosed in infants by testing for the excessive accumulation of fatty acyl groups in the blood and urine due to impaired fatty acid oxidation. This typically involves clinically controlled starvation (Eur. J. Pediatr. (1990) 150:80–850). In cases where infants have not developed hypoglycemia, the infant is deemed free of metabolic disease. As a result, it has become generally accepted that if an infant has total plasma free fatty acid levels, hereinafter referred to as FFA, in the range 1–4 mM their metabolism is considered normal. Unfortunately, to-date, no blood or urine profile is as being indicative of failure to thrive syndrome.

SUMMARY OF THE INVENTION

It is one object of the invention to provide an infant formula for use with infants with metabolic disorders in fatty acid catabolism such as MCAD, LCAD, SCAD, MADD and FTTS.

It is another object of the present invention to provide an assay for diagnosing children and infants with Failure to Thrive Syndrome.

It is another object of the present invention to provide a method for treating Failure to Thrive Syndrome.

It is another object of the present invention to provide a process for normalizing the lipid content of the mitochondrial membrane to prevent carnitine deficiency.

The present inventors have now found that these objects can be achieved with a low fat infant formula which has 90–130 cals/Kg in 100–150 mL/Kg total volume and comprises: (a) 2.5–3.5 g/Kg protein, (b) carbohydrate containing ⅓ simple and ⅔ complex, (c) fat containing ⅓ saturated fat, ⅓ monounsaturated fat, and ⅓ polyunsaturated fat and (d) 50–150 mg/Kg carnitine, such that the non-protein carbohydrate: fat ratio is greater than or equal to 60:40.

Various other objects, features and attendant advantages of the present invention will be more fully appreciated and understood from the following detailed description when considered in connection with the accompanying drawings.

DETAILED DESCRIPTION OF THE PREFERRED EMBODIMENTS

The first embodiment of the present invention provides a low fat infant formula which contains 90–130 cals/Kg in 100–150 mL/Kg total volume and comprises: (a) 2.5–3.5 g/Kg protein, (b) carbohydrate containing ⅓ simple and ⅔ complex, (c) fat containing ⅓ saturated fat, ⅓ monounsaturated fat, and ⅓ polyunsaturated fat and (d) 50–150 mg/Kg carnitine; such that the carbohydrate: fat ratio of the infant formula is greater than or equal to 60:40.

The term "infant" used herein means a child from about 1 day to about 60 months in age. The formula of the present invention is intended for use in infants from about 6 months to up to 5 years in age. Preferably, the formula is used in an infant from about 6 months to 30 months in age.

The formula of the present invention contains 2.5–3.5 g/Kg, preferably 2.5–3.0 g/Kg, protein. The protein can be any supplied in any conventional form such as casein, salts of casein (e.g. potassium caseinate), whey protein concentrate, soybean protein isolate, cow's milk protein, or hydrolyzed whey, or soy protein. Preferably whey and casein are used. Preferably the whey: casein ratio is 70:30. The whey can be prepared to have reduced allergenicity using conventional techniques such as described in U.S. Pat. No. 4,879,131. The whey can also be demineralized for example by electrodialysis or ultrafiltration.

The formula of the present invention provides 80% of its total non-protein calories as carbohydrate. The carbohydrate can be supplied in any conventional form including both simple and complex forms. Preferably, the carbohydrate is provided in ⅓ simple form and ⅔ complex form. Simple carbohydrates include lactose, sucrose, corn syrup solids. Complex carbohydrates include starches. Preferably glucose and starches are used.

The formula of the present invention contains 20% of its total non-protein calories as fat. The fat can be supplied in any conventional form including saturated fats, monounsaturated fats (MUFA), polyunsaturated fats (PUFA) or a mixture thereof. Preferably the fat is provided as ⅓ saturated fat, ⅓ MUFA and ⅓ PUFA. Saturated fats include butyric, valeric, caproic, caprylic, decanoic, lauric, myristic, palmitic, steraic, arachidic, behenic and lignoceric. MUFAs include palmitoleic, oleic, elaidic, vaccenic and erucic. PUFAs include linoleic, α-linolenic (18:3), γ-linoleic (18:2), aracadonic (20:4), eicosopenanoate (20:5) and decosodexanoic (22:6). Preferably, PUFA is supplied as a α-linolenic and linoleic.

The formula of the present invention contains a carbohydrate: lipid ratio which is greater than 60:40. Preferably the ratio of carbohydrate to lipid is between 65:35 and 90:10. More preferably still it is between 70:30 and 85:15, and more preferably still it is 80:20.

The formula of the present invention provides $\geq 50$ mg/Kg carnitine. Preferably the carnitine is provided in unit dosage form in amounts sufficient to maintain the infant's free carnitine levels at around 25–30 mM. More preferably the dosage is from 80 mg to 130 mg/kg/day. Generally, however, a dose of 1 g/day irrespective of age and size is suitable.

The formula of the present invention can additionally contain nutritionally acceptable quantities of the following minerals and vitamins: calcium, phosphorus, potassium, sodium, chloride, magnesium, iron, copper, zinc, manganese, iodine, selenium, vitamin A, vitamin D, vitamin E, vitamin $K_1$, vitamin $B_1$, vitamin $B_2$, vitamin $B_6$, vitamin $B_{12}$, vitamin C, pantothenic acid, niacin, folic acid, biotin, choline, and inositol. The formula can also contain other nutritional factors including taurine, nucleotides, etc.

The formula of the present invention can additionally include pharmaceutically acceptable fillers, color additives, taste modifiers, non-antagonistic antibiotics, pharmaceuticals and medicaments.

The infant formula of the present invention can be in a form suitable for ingestion orally or for administration intravenously. Oral formulations are preferred.

The infant formula of the present invention is suitably formulated to provide 90–130 cals/Kg, preferably 110 cals/Kg. The total volume per dose is 50–200 ml/Kg, preferable 100–150 ml/Kg.

In a second embodiment, the present invention provides an assay for diagnosing children and infants with failure to thrive syndrome which comprises subjecting the child or infant with suspected FTTS to extended fasting, measuring the plasma glucose, free fatty acids and 3-hydroxybutyrate (3HOB) levels, and determining if these levels are outside of normal limits.

Although the metabolic response to extended fasting during infancy has been previously reported from studies in which the patients were being evaluated for suspected hypoglycemia, no analysis exists to diagnosis FTTS. Previous studies have shown that hypoglycemia was not observed after 24 hours fasting and the concomitant levels of plasma FFA were interpreted as normal and physiological. Thus, for children, FFA levels in the range 0.5–4.0 mM (±2SD) have become acceptable. The method of analysis of the present invention demonstrates that there are several different responses to extended fasting in infancy and children. By selecting patients at the more severe end of the FTT spectrum who have failed to respond to previous conventional treatments, the inventors have discovered an efficient method for diagnosing FTTS in infants. Of the cases used, 30/125 (25%) proved to have a normal response, similar to that reported from studies conducted in societies where or at times when elective extended fasting of normal healthy infants was ethically acceptable. A further 16/125 (13%)

proved to have starvation ketosis or ketotic (non) hypoglycemic syndrome for which the precise cause still remains unclear. The remaining 79/125 (63%) represent the true target group of this study.

The indication that these cases harbored a limited capacity to fully degrade fatty acids was the combination of absolute hyperfattyacidemia and relative hypoketonemia. If FAO/KG was fully activated, 3HOB levels of 4–6 mM would be expected (as with starvation ketosis). If fatty acid oxidation-ketogenesis (FAO/KG) was seriously inactivated, 3HOB levels of less than 0.5 mM would be expected (as with inborn errors of FAO). In our cases, the 3HOB levels were intermediate suggesting a partial impairment of FAO. The finding of significant DCAuria gave further confirmation that mitochondrial beta oxidation was impaired in that the alternate pathways of peroxisomal beta and microsomal omega oxidation were activated.

The precise site within mitochondrial beta oxidation that was rate limiting could involve one of four sequential enzymes required to sequentially remove 2 carbon atom fragments from the carboxyl end of the parent fatty acid. These enzymes would be (a) FAD linked dehydrogenase (b) enoylhydratase (c) NAD linked dehydrogenase and (d) ketothiolase. Since 3OH-DCAuria is found in patients with FTTS, the rate limiting step appears to involve the NAD linked dehydrogenase (a.k.a. long chain 3 hydroxy acyl CoA dehydrogenase or LCHAD).

The explanation for significant 3OH DCAuria in cases with normal LCHAD activity remains elusive. In severe cases of 3OH DCAuria without LCHAD deficiency who survive the initial acute crisis, evidence of retinitis pigmentosa, optic atrophy, peripheral neuropathy and hepatic fibrosis has been reported in some cases on long term follow up; evidence for a membranotoxic effect. In 1992, it was reported that LCHAD is not a single enzyme but one component of a dimeric trifunctional enzyme protein (TEP) comprising combined hydrate, dehydrogenase and thiolase activities and which is bound to the inner mitochondrial membrane. In hyperfattyacidemic cases with 3–4+ 3OH DCAuria, we detected accumulations of mono-unsaturated forms as the substrate for the hydratase and 3 keto forms as the substrate for the thiolase. These observations implicate the integrity of TEP complex as a whole rather than just the LCHAD component.

Further evaluation of the urinary organic acid profile suggests that other NAD requiring dehydrogenase activities are also involved; namely B-CHAD and isocitrate/malate dehydrogenases. NAD is also a key cofactor of the dihydrolipoyl dehydrogenase (E3) component of the multienzyme complexes such as pyruvate, 2-ketoglutarate and 2-ketoadipate dehydrogenases as well as the glycine cleavage system.

A final metabolite in the organic acid profile which would be considered is 3 methyl glutaconate (3MGC). Recently defects of both the respiratory chain and of cholesterol biosynthesis have been reported in cases of MGC uria. A common link appears to be coenzyme Q which is both a cofactor of Complex 1 (NADH-CoQ reductase) of the respiratory chain and a product of cholesterol/isoprenoid biosynthetic pathway.

The metabolite perturbation in infants with FTT is a very complicated one. It is unlikely that the primary defect involved LCHAD (or TFE) unless the associated genetic variability and polymorphisms of the enzyme protein are incredibly common. It is unlikely that the primary defect involved NADH-CoQ reductase causing a secondary deficiency in LCHAD activity due to reduced NAD availability. If this were the case, hyperlacticacidemia, further exacerbated by the high carbohydrate component of the therapeutic diet, would have been observed. It is unlikely that the primary defect involved nicotinamide availability because clinical improvement occurred without niacin replacement. The most likely primary defect therefore appears to be an abnormality of inner mitochondrial membrane structure that adversely affects the binding, assembly and hence expression of multiple enzyme activities. The initial membranopathy is probably related to an inappropriate fatty acid profile of previously consumed infant formulas that affects the phospholipid composition of the membrane. This then impairs LCHAD activity with resultant accumulation of 3 hydroxyfattyacids that cause further membranal problems—thus setting up a self perpetuating hostile metabolic environment.

In a third embodiment, the present invention provides a method for treating failure to thrive syndrome. The method comprises administering the infant formula described above.

In a fourth embodiment, the present invention provides a process for normalizing the lipid content of the mitochondrial membrane to prevent carnitine deficiency. The method comprises normalizing the fatty acids in the mitochondrial membrane through a diet comprising the infant formula described above or a diet containing a minimum fat content of 30–37% of total calories and carnitine levels which provide at least 50 mg/Kg.

Having generally described this invention, a further understanding can be obtained by reference to certain specific examples which are provided herein for purposes of illustration only and are not intended to be limiting unless otherwise specified.

EXAMPLES

Patients

A total of 125 cases were evaluated. Group A comprised 85 infants in the 6 to 30 months age range (mean 13 m). In half the dominant feature was recurrent vomiting and they had been diagnosed and treated as cases of gastroesophageal reflux (with 12 having undergone fundoplication surgery with poor results). In the remaining cases, muscle weakness and motor delay were the dominant features. These infants were receiving physical and occupational therapy as treatment of presumed central hypotonia. Speech therapy was commonplace to improve oromandibular swallowing function. Of these 85 infants, 25% were below 2.5 Kg at birth, predominantly due to prematurity. For all infants growth faltering below the expected trajectories had commenced at 4–6 months of age. Of the 75% who were above 2.5 Kg at birth, 60% were to fall below the 5th percentile and 15% remained within the normal range but had dropped over two standard percentile trajectory lines. The older infants in this group exhibited early evidence of speech and language delay.

Group B comprised of 40 children in the 3–9 year age range (mean 5 years). These cases had all suffered combined recurrent vomiting and muscle weakness in earlier life as with Group A infants. These features were still present to variable degrees. All had required speech-language therapy for cognitive delays. Most of the older ones were in special education classes for learning disabilities. About half were generally placid and apathetic, exhibiting withdrawn personalities. The other half exhibited hyperactive behavior and had or were receiving Ritilin therapy. All these children were at or below the 5th percentile for weight at the time of study.

Methods

Fasting protocol

All cases were admitted to hospital for evaluation at a time of no supervening fever or infections. Their usual evening meal was provided at 6:00 pm and thereafter they received only water ad lib until conclusion of the study. Plasma samples (2 ml) were obtained at 9:00 am, 12 noon and 3:00 pm the following day; equating to 15, 18 and 21 hour fasting. The next urine sample passed after 3:00 pm was saved, together with a urine sample collected the previous evening. Throughout, the patient was under constant supervision by a parent and intermittent observation by ward nurses and metabolic nurse practitioner. The study was to be concluded if evidence of excessive lethargy developed but this was found not to be necessary. Occasionally biochemical evidence that was being sought was evident in the 12 noon sample, whereupon the study was concluded. Occasionally, an additional sample was obtained at 4:30 pm, if the 3:00 pm sample gave inconclusive results. Upon conclusion of the study, the patient was fed his/her regular meal. In 6 cases, this was not retained due to vomiting whereupon IV glucose was administered for 1–2 hours before refeeding with success.

Laboratory Analyses

Each plasma sample was analyzed, in duplicate, for glucose (G), free fatty acids (FFA), 3 hydroxybutyrate (3HOB) with results becoming available within 60 minutes of benepuncture. G, and 3HOB were measured by standard enzymatic spectrophotometric methods. FFA was measured by the method of Duncombe WG, Clin. Chim. Acta (1964) 9:122 or Itaya K, J. Lipid Res. (1965) 6:16 using a WACO NEFA-C™ test kit. Within the next 2–3 days, the remaining plasma sample was analyzed for total and free carnitine content by the method of McGarry and Foste and the urine samples were analyzed for organic acid profile.

Diet Protocol

Key results of the biochemical analyses were available the same day and, if indicated, the patient was discharged with the recommendation to initiate an isocaloric fat restricted-carbohydrate enriched diet. This diet provided 100 kcals/Kg/day with 2.5–3.0 gms protein/Kg/day. Of the remaining calories, 20% were provided as fat and 80% as carbohydrate, two third as complex carbohydrate. For the Group A infants, this diet was provided in the form of a milk formula by taking a proprietary commercial regular infant formula and diluting in half the fat content by adding carbohydrate. In so doing, the protein, vitamin and mineral contents were also diluted but then were recorrected to satisfy RDA values by appropriate supplementations. For the Group B children, this milk formula provided about 30–50% of total caloric intake with the remainder comprising various pureed and solid foods according to a menu designed to maintain the same fat:carbohydrate caloric ratio. With increasing age, Group A infants were gradually introduced to the diet for Group B children. At the first follow up appointment, 2–3 months after initiation of the diet, L-carnitine supplementation was commenced at a dose of 250 mg Q.I.D.

These cases were then evaluated every 4–6 months with particular reference to (a) status of recurrent vomiting and/or muscle weakness (b) changes in body growth and () emergence of neurodevelopmental delays.

Results

1. Biochemical Analysis (a) Plasma Metabolites (G, FFA, 3HOB)—Table 1

Intermittently during the study, available data was analyzed. It became evident that although trends could be determined in the samples obtained after 15 and 18 hours fasting, statistically significant data that allowed subcatergorization (see below) of cases became available only in the samples obtained at 21 hours fasting—only this data is presented. Group A of the 85 infants, 60 (70%) attained FFA levels in excess of 2.5 mM (2.86±0.65 mM) with 3HOB levels of 3.3±1.08 mM. There was no difference between the 30 with predominant vomiting and the 30 with predominant muscle weakness. Of the remaining 25 infants, 10 (12%) developed 3HOB levels in excess of 4 mM (5.10±0.76 mM) with FFA levels below 2.5 mM (1.85±0.25 mM). The latter group were designated hyperketonemic (HK) with fully activated intact fatty acid oxidation (FAO) and ketogenesis (KG). The former group were designated hyperfattyacidemic (HF) with a reduced capacity for fatty acid oxidation (absolute hyperfattyacidemia) and ketogenesis (relative hypoketonemia). Glycemic status was equivalent in both groups, 2.49±0.71 compared to 2.72±0.62 mM respectively. The remaining 15 cases (18%) were designated controls. Group B by the same criteria of the 40 children studied, 19 (48%) were designated hyperfattyacidemic, 6 (15%) were designated hyperketonemic and 15 (37%) were designated controls.

(b) Urine Organic Acid Profile

In controls, there was minimal evidence of increased excretion of 3-hydroxybutyrate and acetoacetate i.e. 0–1+ ketonuria. In the hyperketonemic group, there was considerable 4+ ketonuria with minimal increased excretion of saturated medium chain C6–10 dicarboxylates, i.e., 0–1+ DCAuria.

In the hyperfattyacidemic group, significant abnormalities were observed in the post fast sample that were completely absent in the pre fast sample. With prior knowledge of the plasma findings, 3–4+ ketonuria and DCAuria were expected and found in all cases. The key finding was increased excretion of saturated C6–14 3-hydroxylated dicarboxylates (3OH DCAuria) in 1+ to 4+ range. In those cases with 3–4+3OH DCAuria, additional metabolites were identified in small (1–2+) but significant amounts. These were (a) monounsaturated 3-hydroxy and saturated 3-keto dicarboxylates (b) the combination of 3-hydroxyisobutyrate, 2-methyl-3-hydroxybutyrate, tiglyglycine and 2-ethylhydracylate all substrates for branched chain acyl CoA dehydrogenase (B-CHAD) involved in valine and isoleucine degradation, (c) isocitrate and malate in excess of other TCA cycle intermediates (d) 3-methylglutaconate and, its reduced form, 3-methylglutarate. There was no evidence of increased excretion of various acylglycine conjugates (e.g., hexanoyl, butyryl, suberyl glycine or ethylmalonate/methylsuccinate) to suggest a defect at the FAD linked dehydrogenase level.

(c) Plasma Carnitine Profiles (Table 3)

In the 30 control cases (15 Group A infants and 15 Group B children), the mean plasma free/total carnitine ratio declined from 70% to 60% during the period of fasting as the mean acylated/free ratio increased from 0.34 to 0.55.

In the 79 HF cases (60 Group A and 19 Group B children), the mean plasma free/total carnitine ratio declined from 60% to 40% during the period of fasting as the mean acylated/free ratio increased from 0.72 to 1.56.

There was no statistical difference between Group A and Group B either for HF or control cases; the data is presented in combined fashion.

Results

1. Effect of diet on vomiting and weakness

Of the 79 HF cases identified, adequate follow up data became available in 62 cases. Non compliance with dietary recommendations and/or failure to maintain follow up appointments occurred in 11/60 (18%) of Group A HF infants and 6/19 (31%) of Group B HF children.

In the 49 Group A HF infants, 26 had presented with predominant vomiting and 23 with predominant muscle weakness.

Within 7–10 days of initiating the modified diet, 21/26 vomiting infants had completely ceased to vomit and in the remaining 5/26, the frequency of vomiting was considerably reduced. In 4 cases fundoplication surgery with G-tube placement, that had been planned prior to metabolic evaluation, was cancelled. In 6 cases, that had undergone previous surgical intervention, G-tube feedings were found to be no longer necessary.

Within 2 months of initiating the modified diet, 15/23 weak infants exhibited considerable improvements in muscle strength and general activity, gaining, on average, 4 months gross motor development within this time period.

These marked improvements were evident at the first follow up visit after initiating the diets. At that point, carnitine supplementation was commenced. Three months later, additional improvements were reported in 30/49 (61%) cases that parents attributed to carnitine rather than the diet. 5/8 infants with muscle weakness that had not responded to diet change alone now showed improvement. Parents reported improved awareness, sociability and curiosity—"he/she is a different child" and refused any suggestion for a temporary cessation of carnitine to determine its true therapeutic effect.

The 13 Group B children with combined persistent vomiting and weakness similar improvements were observed with cessation of vomiting in 11/13 and improved general activity in 10/13.

2. Effect of diet on growth

Growth rates were normalized in all cases in the 6–12 months following institution of the diet. Those that were below 2.5 Kg at birth, and had remained below the 5th percentile regained a growth trajectory at or just below that percentile (N=15/62 or 25%). Those that were between the 25th and 75th percentile at birth but had crossed two percentile lines regained their original percentile (n=9/62 or 15%). The remaining cases (n=38/62 or 60%) that had started off within the normal range but had fallen below the 5th percentile fell into two groups, half regained a percentile trajectory within the normal range and the other half gained a percentile trajectory closer to or at the 5th percentile. This divergence could not be accounted for by duration or severity of FTT prior to initiation of the modified diet.

3. Effect of diet on neurodevelopment

In retrospect it is unfortunate that infants and children involved in this study were not formally tested for neurodevelopmental status prior to and then intermittently during dietary therapy. However, whereas all Group B children at the mean age of 5 years upon starting diet therapy, exhibited evidence of significant speech-language delays, learning impairment and behavioral disturbance, it is clear that those Group A cases that were 2–2½ years when the modified diet was started and have been followed up for 2½–3 years, i.e., are presently 4½–5½ years of age do not exhibit the same extent of neurodevelopmental impairment. Amongst the Group B children, several were moved from special education classes to regular grade classes in the 1–2 years following institution of diet therapy. These are preliminary observations to be confirmed by additional prospective studies.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by letters patent of the United States is:

1. An infant formula, comprising 90–130 cal/Kg, wherein said formula comprises:
   (a) 2.3–3.5 g/Kg protein;
   (b) carbohydrate;
   (c) fat; and
   (d) ≧500 mg carnitine,
   wherein the ratio of carbohydrate to fat is greater than or equal to 60:40.
2. The infant formula according to claim 1, wherein said ratio of carbohydrate to fat is between 65:35 and 90:10.
3. The infant formula according to claim 2, wherein said ratio of carbohydrate to fat is between 70:30 and 85:15.
4. The infant formula according to claim 3, wherein said ratio of carbohydrate to fat is 80:20.
5. The infant formula according to claim 1, wherein said carbohydrate comprises ⅓ simple form and ⅔ complex form.
6. The infant formula according to claim 1, wherein said fat comprises ⅓ saturated fat, ⅓ monounsaturated fat, and ⅓ polyunsaturated fat.
7. The infant formula according to claim 5, wherein said simple form of carbohydrate is glucose.
8. The infant formula according to claim 5, wherein said complex form of carbohydrate is a starch.
9. The infant formula according to claim 6, wherein said polyunsaturated fat is α-linolenic, linoleic or a mixture thereof.
10. The infant formula according to claim 1, which comprises ≧1000 mg of carnitine.
11. An infant formula containing 110 calories/Kg which comprises:
   (a) 2.5–3.0 g/Kg of protein, wherein said protein is 70 weight % whey and 30 weight % casein based on the total weight of protein;
   (b) carbohydrate comprising ⅓ simple form and ⅔ complex form;
   (c) fat comprising ⅓ saturated fat, ⅓ monounsaturated fat and ⅓ polyunsaturated fat;
   (d) 1000 mg carnitine; and
   (e) optionally, minerals and vitamins.
12. A method of treating Failure to Thrive Syndrome (FTTS), comprising administering to a patient in need thereof a formula which contains 90–130 cals/Kg and comprises:

(a) 2.5–3.5 g/Kg protein;

(b) carbohydrate;

(c) fat; and (d) ≧500 mg carnitine, wherein the ratio of carbohydrate to fat is greater than or equal to 60:40.

13. The method of claim 12, wherein said patient is 6 months to 5 years in age.

14. The method of claim 12, wherein said administering is continued for at least 1 month.

15. A method for returning the lipid content of the mitochondrial membrane to homeostasis comprising:

administering a composition containing:

(a) carbohydrate;

(b) saturated fat: monounsaturated fat: polyunsaturated fat in a 1:1:1 weight ratio; and (c) ≧500 mg carnitine, wherein the ratio of carbohydrate to fat is greater than or equal to 60:40.

16. The method of claim 15, wherein said polyunsaturated fat is linoleic and α-linolenic.

17. An infant formula, comprising 90–130 cal/Kg, wherein said formula comprises ≧500 mg carnitine and 2.3–3.5 g/Kg protein and the remaining calories are provided as carbohydrate and fat; and wherein the ratio of carbohydrate to fat is greater than or equal to 60:40.

18. The infant formula of claim 17, wherein the remaining calories are provided as 80% carbohydrate and 20% fat.

19. The infant formula of claim 17, wherein the fat comprises ⅓ unsaturated fat, ⅓ polyunsaturated fat and ⅓ monounsaturated fat.

* * * * *